United States Patent [19]

Carle et al.

[11] 4,143,086

[45] Mar. 6, 1979

[54] FLUID CATALYTIC CRACKING OF AMORPHOUS POLYPROPYLENE

[75] Inventors: Robert A. Carle; Paul D. Hann, both of Bartlesville, Okla.

[73] Assignee: Phillips Petroleum Company, Bartlesville, Okla.

[21] Appl. No.: 792,831

[22] Filed: May 2, 1977

[51] Int. Cl.² ............................................... C07C 3/26
[52] U.S. Cl. .............................. 260/683 PD; 208/113
[58] Field of Search ................. 260/683 PD; 252/411; 208/119, 113

[56] References Cited

U.S. PATENT DOCUMENTS

| | | | |
|---|---|---|---|
| 2,385,326 | 9/1945 | Bailey | 260/683 PD |
| 2,514,332 | 7/1950 | Murphree | 260/683 PD |
| 2,897,136 | 7/1959 | Pardee | 208/119 |
| 3,000,990 | 9/1961 | Hill et al. | 260/683 PD |
| 3,750,600 | 8/1973 | Oshol et al. | 260/683 PD |

*Primary Examiner*—Delbert E. Gantz
*Assistant Examiner*—Charles E. Spresser

[57] ABSTRACT

The propylene values of waste, amorphous polypropylene are recovered at least in part, by charging amorphous polypropylene together with a hydrocarbon feedstock to a catalytic cracking unit.

7 Claims, 1 Drawing Figure

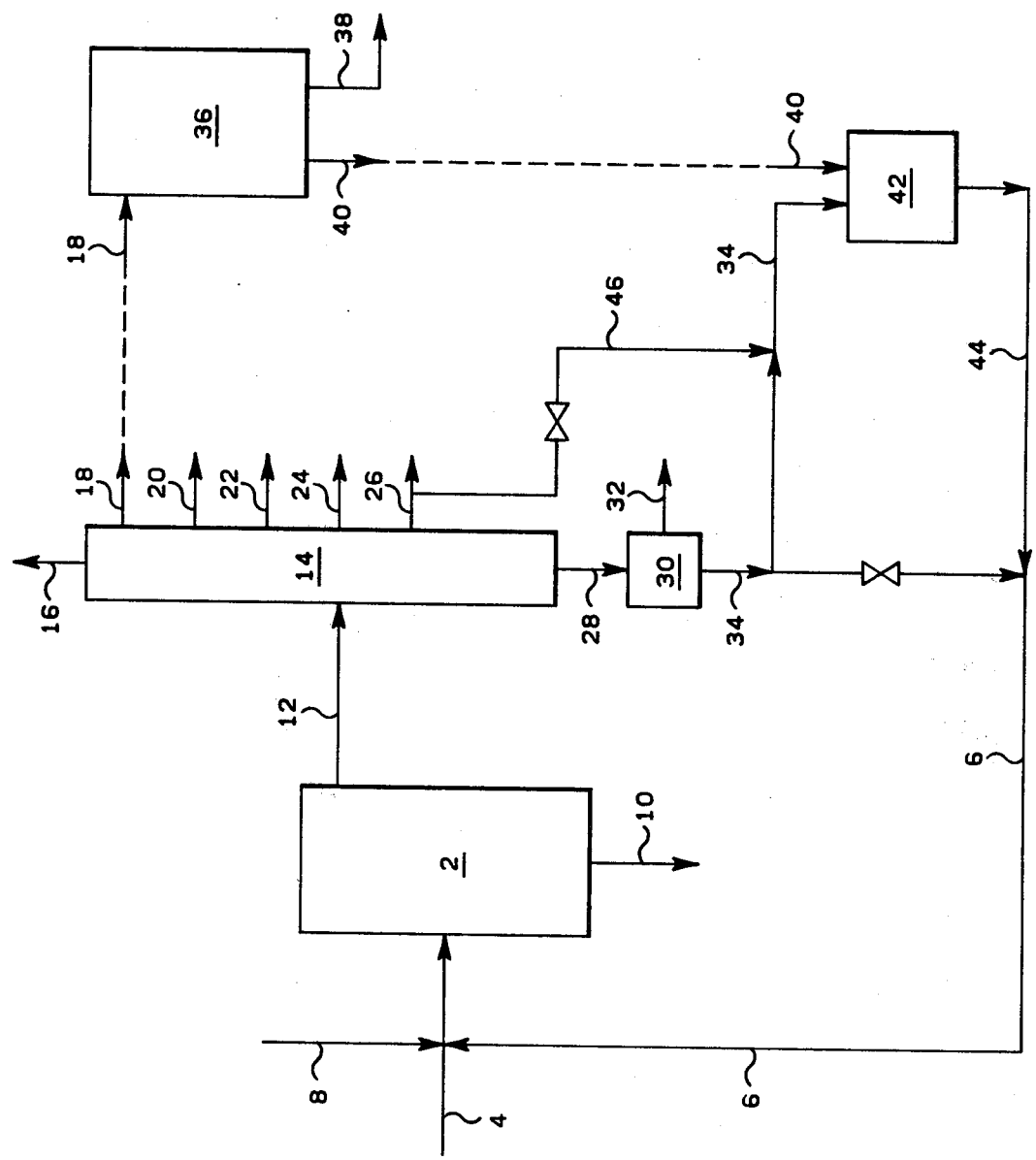

FLUID CATALYTIC CRACKING OF AMORPHOUS POLYPROPYLENE

This invention relates to a catalytic cracking process.

In the production of stereo-regular polypropylene, there is produced a small amount of amorphous polypropylene as a disposable by-product. Various attempts have been made to either reduce the amount of by-product amorphous polypropylene by the use of specific catalysts, or to make use of the by-product, as for example, an oil-absorbing agent, or a land-reclaiming material. The most common disposal method, is to burn the amorphous polypropylene, with or without recovery of the heat values therefrom. Disposal of this by-product by burning often represents a complete waste, not only of the propylene values of such polymer, but also of the heat value therefrom, since such heat is generally not needed.

Accordingly, it is an object of the present invention to provide a process for disposing of by-product amorphous polypropylene.

It is another object of this invention to provide a process for deactivating at least a portion of the metal-containing poisons accumulated on used cracking catalysts.

Other objects, aspects and advantages of the present invention will be apparent to those skilled in the art from a reading of the following detailed description of the invention.

In accordance with the present invention, at least a portion of the propylene value of by-product amorphous polypropylene is recovered by employing such polymer as at least a portion of the feed to a catalytic cracking process so that the amorphous polypropylene is converted, at least in part, to propylene.

In accordance with another embodiment of the present invention, there is provided a process for simultaneously adding titanium to a cracking catalyst during a catalytic cracking process, thereby deactivating at least a portion of the metal-containing poisons accumulated on used cracking catalysts, and for recovering at least a portion of the propylene value from amorphous polypropylene which comprises charging an amorphous polypropylene containing titanium polymerization catalyst residues as at least a portion of the feed to a catalytic cracking process.

The process of this invention can be carried out in that equipment and under those operating conditions conventionally employed to catalytically crack a hydrocarbon feedstock, such as the catalytic cracking apparatus disclosed in U.S. Pat. Nos. 3,164,542 and 3,305,475.

The amorphous polypropylene is introduced in solution into the catalytic cracking zone together with the conventional hydrocarbon feed to such zone.

The process of this invention will be better understood by reference to the drawing which is a schematic representation of this process.

Referring now to the drawing, a hydrocarbon feed stream is fed to a catalytic cracking zone 2 by way of line 4. The recycle hydrocarbon stream (e.g., heavy cycle oil or slurry oil) which can be introduced by way of line 6, together with the fresh feed in line 4, make up the total feed to the catalytic cracking zone 2. A heater, not shown, heats the fresh feed and recycle streams to a temperature slightly under that at which thermal cracking might occur prior to admission to the cracking zone 2. Hot regenerated catalyst is added to the catalytic cracking zone 2 by way of line 8 and used catalyst is removed by way of line 10 and passed to a regeneration zone (not shown) and is then returned to the catalytic cracking zone 2 at a temperature higher than the catalytic cracking temperature so that the mixture of heated oil and regenerated catalyst achieves the desired cracking temperature in the cracking zone.

The catalyst can be any desired type of cracking catalyst, such as, for example, a silica-alumina cracking catalyst, a zeolitic type cracking catalyst, or mixtures thereof. Also, in the embodiment of the invention presently described, the catalytic cracking reactors are of the fluidized flow type employing a finely divided catalyst. A regenerator, also employing the fluid-solids flow technique, along with the cracking reactor, fractionating facilities and other facilities make up the system known in the art as a Fluid Catalytic Cracking (FCC) unit.

The hydrocarbon effluent from the catalytic cracking zone 2 is passed through line 12 to product fractionator zone 14 wherein the effluent products are separated into fractions having different boiling ranges from whence light gases are removed by way of line 16, a propylene cut is removed by way of line 18, a propane/$C_4$ cut is removed by way of line 20, a gasoline cut is removed by way of line 22, a light cycle oil is removed by way of line 24 and a heavy cycle oil is removed by way of line 26 to form the various products of the process.

The total bottoms product, including catalyst fines carried over from catalytic cracking unit 2, is removed from the base of fractionator 14 by way of line 28. If desired, the bottoms product can be decanted, either in fractionator 14 or, as shown, using an external decanter 30, e.g., Dorr thickener. The decant oil is removed from the decanter 30 by way of line 32. The slurry oil is removed by way of line 34 and passed to a mixing zone 42.

In the embodiment shown, the propylene in line 18 is passed to a separate polypropylene manufacture and separation zone 36, wherein the propylene is polymerized in a polymerization reactor in the presence of a suitable polymerization catalyst or catalyst system, such as, for example, a catalyst system comprising an an alkylaluminum halide compound, such as dialkyl aluminum chloride and a titanium compound such as the reduction product of reaction of titanium tetrachloride and aluminum according to polymerization procedures well known in the art. When the desired degree of polymerization is achieved, the reactor contents are treated to deactivate the polymerization catalyst. The polymer is then treated to remove catalyst residues associated therewith. A complete description of the actual polymerization operation and treatment to remove the catalyst is given in U.S. Pat. No. 3,280,090, issued Oct. 18, 1966. A description of a process for concentrating catalyst residues in the soluble polymer, i.e., amorphous polypropylene, is given in U.S. Pat. No. 3,257,372, issued June 21, 1966.

Referring again to the drawing, polypropylene product is withdrawn from the polypropylene manufacture and separation zone 36 by way of line 38. The amorphous polypropylene, containing catalyst residues, is withdrawn from zone 36 by way of line 40.

The amorphous polypropylene is passed through line 40 to mixing zone 42 wherein it is at least partially dissolved in the slurry oil. The quantity of amorphous polypropylene dissolved in the slurry oil can range from 0.5 to about 10 volume percent. The mixing zone 42 is provided with suitable heating means and mixing means. The slurry oil/amorphous polypropylene mixture is withdrawn from mixing zone 42 by way of line 44 and passed to recycle line 6.

If desired, a portion of the heavy cycle oil in line 26 can be passed through line 46 to mixing zone 42 to further dilute the slurry oil/amorphous polypropylene mixture.

The feed to catalytic cracking zone 2 can be a topped crude, a virgin gas oil, or other suitable conventional feedstock.

The quantity of amorphous polypropylene charged to the catalytic cracking zone 2 ranges from about 0.01 to about 1 volume percent, or greater, based upon the feed to cracking zone 2. Greater amounts, i.e., up to about 2.5 percent or greater, can be charged to cracking zone 2, as necessary, to minimize storage requirements for the amorphous polypropylene.

The amorphous polypropylene can be transported from the manufacture and separation zone 36 to the mixing zone 42 by heated pipe line or heated tank car, or other suitable means.

As mentioned previously, one advantage of the present invention is that the propylene value can be recovered from the amorphous polypropylene. Another advantage of the present invention is that the titanium catalyst residue in the amorphous polypropylene will assist in deactivating metal-poisoned cracking catalysts, as disclosed by U.S. Pat. No. 3,696,025. For example, an amorphous polypropylene containing about 11,000 ppm of titanium, when charged at the rate of 0.5 percent of the feed to a catalytic cracking zone should deposit about 7 ppm by weight (about 30 pounds/hour titanium) of titanium per hour on the cracking catalyst.

Reasonable variations and modifications, which will be apparent to those skilled in the art, can be made in this invention without departing from the spirit and scope thereof.

What is claimed is:

1. A process comprising:
   charging a mixture of amorphous polypropylene containing a titanium catalyst residue and a hydrocarbon feedstock to a catalytic cracking unit, said amorphous polypropylene being present in an amount up to about 2.5 volume percent, based upon the feed to said unit; and
   contacting the mixture of amorphous polypropylene and feedstock with a catalyst in the catalytic cracking unit to produce an effluent comprising propylene,
   wherein the cracking catalyst in the catalytic cracking unit is in contact with at least one metal capable of poisoning the catalyst and wherein the titanium catalyst residue in the amorphous polypropylene deactivates at least a portion of the at least one metal that is capable of poisoning the catalyst.

2. A process according to claim 1 wherein said titanium catalyst residue is the reduction product of the reaction of titanium tetrachloride and an alkylaluminum halide compound.

3. A process according to claim 1 wherein said titanium catalyst residue is the reduction product of the reaction of titanium tetrachloride and a dialkyl aluminum chloride compound.

4. A process according to claim 3 wherein the amount of titanium catalyst residue in the amorphous polypropylene is approximately 11,000 parts per million parts of amorphous polypropylene.

5. The process of claim 1 wherein the effluent from said cracking unit is fractionated to at least obtain a propylene cut, a gasoline cut, a light cycle oil, a heavy cycle oil and a bottoms product, wherein said bottoms product is decanted to obtain a decant oil and a slurry oil, and wherein said amorphous polypropylene is thereafter at least partially dissolved in said slurry oil and wherein the resulting mixture of slurry oil and amorphous polypropylene is charged to said catalytic cracking unit together with said feedstock.

6. The process of claim 5 wherein the amount of said amorphous polypropylene in said slurry oil ranges from 0.5 to about 10 volume percent.

7. The process of claim 1 wherein said hydrocarbon feedstock is a virgin gas oil.

* * * * *